Figure 1:
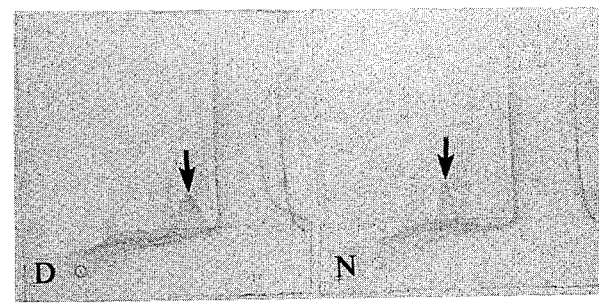

United States Patent [19]

Kerkay

[11] Patent Number: 4,818,708

[45] Date of Patent: Apr. 4, 1989

[54] CROSSED IMMUNOELECTROPHORETIC TECHNIQUE FOR PREDICTING DOWN'S SYNDROME OCCURRENCE

[76] Inventor: Julius Kerkay, 8040 Barbara Dr., Strongsville, Ohio 44136

[21] Appl. No.: 736,352

[22] Filed: May 21, 1985

[51] Int. Cl.$^4$ .......................................... G01N 33/561
[52] U.S. Cl. ..................................................... 436/516
[58] Field of Search ........................................ 436/516

[56] References Cited

PUBLICATIONS

P. O. Ganrot, *Scand. Journ. Clin. Lab. Invest.*, 29, Suppl. 124, pp. 39–47, 1972.

G. Kwapinski, *Methodology of Investigative and Clinical Immunology*, Robert E. Krieger Publishing Co., Inc., Malabar, FL, 1982, pp. 306–310.

O. Ouchterlony et al., in D. M. Weir (Ed), *Handbook of Experimental Immunology*—3rd Ed., Blackwell Scientific Pub., Oxford, 1978, p. 19.31.

J. Nedziora et al., *Experientia*, 36, 926–927, 1980.

J. F. Monthony et al., *Clin. Chem.*, 24, 1925–1827, 1978.

B. Weeke, *Scand Journ Immunol*, 2 (Suppl 1), 47–56, 1973.

J. Kerkay et al., *American Journ. Ment. Defil.*, 75, 729–732, 1971.

*Primary Examiner*—Sam Rosen
*Assistant Examiner*—David A. Saunders
*Attorney, Agent, or Firm*—Woodling, Krost & Rust

[57] ABSTRACT

An improved crossed electrophoretic technique is disclosed, which is especially adapted for detecting the presence in serum of a protein associated with parenting a Down's syndrome child. The improved technique comprises reducing the second dimension gel antiserum concentration and increasing the second dimension voltage, to be within certain limits.

2 Claims, 1 Drawing Sheet

CROSSED IMMUNOELECTROPHORETIC TECHNIQUE FOR PREDICTING DOWN'S SYNDROME OCCURRENCE

This invention relates to prediction and diagnosis by assay of blood serum proteins. In particular, it relates to a crossed immunoelectrophoretic technique for detecting the presence in serum of a protein associated with parenting a Down's syndrome child.

BACKGROUND OF THE INVENTION

Down's syndrome, the major cause of congenital mental retardation, is also the most common birth defect in man. It was traditionally called "mongolism", a name which has fallen from favor. In addition to the more modern name, Down's syndrome, this anomaly is often referred to as trisomy 21. Whereas "Down's syndrome" is used to describe those individuals who present certain clinical features, the term, trisomy 21, refers to the presumed chromosomal basis for these features. Over 90 percent of the individuals affected with Down's syndrome have an extra number 21 chromosome in their cells.

Trisomy 21 results from nondisjunction or failure of chromosomes to separate sometime during either division of meiosis or mitosis. Most Down's syndrome individuals have trisomy 21, and conversely, in individuals who carry a translocation involving chromosome 21, and in mosaics who have both trisomic and normal cells, the characteristics of the syndrome are seen.

The frequency of Down's syndrome births has been strongly correlated to advanced maternal age. However, there appear to be two types ("A" and "B") of Down's syndrome, only one of them correlated with maternal age. And nondisjunction in the father can lead to a trisomy 21 child. Evidently factors different from those identified with age may operate to give a Down's syndrome genotype.

Regardless of the occurrence of Down's syndrome births to young mothers, the strong statistical correlation between increased frequency of Down's syndrome births and advanced maternal age has been the conventional basis for predicting the risk of giving birth to an affected child. Recent reports, however, cast doubt upon this practice. Several researchers have found a decrease in frequency of all births to older women during the 1960 to 1975 period, but a concomitant decline in Down's syndrome was not found. Holmes (Holmes, L. B. Genetic Counseling for the Older Pregnant Woman; New Data and Questions. *N England J Med* 298, 1419-1421 (1978)), in his study for the Massachusetts Department of Public Health, stated that while women younger than 35 years old are having 90 percent of all infants, they are also having 65 to 80 percent of all Down's syndrome infants. In these infants, the syndrome is associated with trisomy 21 with the same high frequency as in children of older mothers. Thus, it appears that the observed increase in frequency of Down's syndrome births to young mothers reflects an increase in trisomy 21 or nondisjunction.

Resolution of the problems surrounding the etiology of Down's syndrome is difficult. Advancing maternal age is apparently only one condition that provides an environment conducive to nondisjunction. In particular, many studies suggest that the tendency toward nondisjunction may be inherited, though a gene specific for nondisjunction has not yet been found. The possibility that action of a specific gene results in nondisjunction would account for a small minority of total Down's syndrome births (Alfi, O. S., Chang, R., Azen, S. P. Evidence for Genetic Control of Nondisjunction in Man. *Am J Hum Genet* 32, 477-483 (1980)). Nonspecific chromosomal abnormalities have been shown to be associated with the nondisjunction phenomenon, though mechanisms of how they exert their effects have not been suggested. For counseling purposes, the presence of chromosomal abnormalities in the parents would certainly help in ascertaining the risk of giving birth to a trisomy 21 child. Routine chromosome analysis, however, would be expensive, difficult to interpret, and, therefore, is not ordinarily advocated.

While seeking the causes of trisomy 21, investigators have studied a variety of biochemical factors that might promote nondisjunction. Those studies have been motivated, in part, by the need for a better way to predict a propensity toward nondisjunction than by citing maternal age statistics or performing cumbersome chromosome analyses.

For example, Down's syndrome individuals' high susceptibility to infections, particularly respiratory infections, provided the basis for various immunological studies. (Rowe, M. J. III, Agranoff, B. W., Tourtellotte, W. W. Immunoelectrophoretic Study of Serum Proteins in Mongolism. *Neurology* 16, 714-719 (1966); Lange, C. F., Justice, P., Smith, G. F. Milk Precipitins in Mongolism. *Res Commun Chem Pathol Pharmacol* 7, 605-612 (1974); Gershwin, M. E., Crinella, F. M., Castles, J. J., Trent, J. K. T. Immunological Characteristics of Down's Syndrome. *J Ment Defic Res* 21, 237-247 (1977); Fekete, G.; Kulcsar, G., Dan, P., Nasz, I., Sculer, D., Dobos, M. Immumological and Virological Investigations in Down's Syndrome. *Eur J Pediatr* 138, 59-62 (1982); Jacobs, P. F., Burdash, N. M., Manos, J. P., Duncan, R. C. Immunologic Parameters in Down's syndrome. *Ann Clin Lab Sci* 8, 17-22 (1978)). It appears from these investigations that the immunological differences between Down's syndrome and normal groups are directly related to the syndrome and its genetic origin rather than to varying degrees of exposure to infections.

In 1971, Kerkay et al. (Kerkay, J., Zsako, S., Kaplan, A. R. Immunoelectrophoretic Patterns Associated with Mothers of Children Affected with $G_1$-trisomy (Down's syndrome). *Am J Mental Deficiency* 75, 729-732 (1971)) reported the presence of an extra precipitin arc in the gamma-A region of immunoelectrophoretic patterns in the sera of 46 of 48 mothers of trisomy 21 children. This same precipitin arc was found in only 10 of 48 age-matched control mothers. In a later article, Kerkay et al. (Kerkay, J., Zsako, S., Cotton, J. E., Kaplan, A. R. Biochemical and Genetic Variables Associated with Mothers of $G_1$-trisomy Affected Children. *Acta Genet Med Gemellol* 24, 239-244 (1975)) described the use of three variables—familial mental retardation, acrocentric chromosome association, and the presence of the extra precipitin line—as a tool of genetic counseling in assessing the potential risk for giving brith to trisomy 21 children.

The extra precipitin arc observed by Kerkay et al. indicates the presence of a protein. That this protein should be found more frequently in the sera of mothers of Down's syndrome children than in the sera of mothers of unaffected children is significant. Not only may the protein be tied to the etiology of trisomy 21, but it seems to be an indicator of a higher potential of bearing a Down's syndrome child.

SUMMARY OF THE INVENTION

Crossed immunoelectrophoresis (CIE) is a two dimensional technique that involves separation of proteins by electrophoresis in one direction, with subsequent electrophoresis, perpendicular to the first, into an antibody-containing gel. As the separated proteins slowly move into the antibody-containing gel, antigen-antibody reactions cause precipitates to form. The result is a series of precipitin peaks that represent serum proteins.

The present invention is an improvement upon the procedure for crossed immunoelectrophoresis given by Weeke (Weeke, B. Crossed Immunoelectrophoresis. In *A Manual of Quantitative Immunoelectrophoresis. Methods and Applications,* N. H. Axelsen, J. Kroll, B. Weeke, Eds., *Scand J Immunol* 2 (suppl 1), 1973, pp. 47–59)). The improvement comprises certain variations in the conditions which greatly increase sensitivity and resolution for the Down's syndrome protein (DSP). In particular, the overall effect of reducing the gel antiserum concentration from 12.5 µL to about 3.1 µL per cm$^2$ and increasing the voltage applied in the second dimension from one to two volts per cm to about eight volts per cm for about 24 hours provides a pattern that can easily be evaluated for Down's syndrome protein. The protein cannot easily be detected at voltages less than about six volts per cm.

Thus, it is an object of this invention to provide an improved method of crossed immunoelectrophoresis which increases resolution of a mixture of proteins.

A further object of the invention is to provide a new method of detecting the presence of Down's syndrome protein in blood serum.

Yet another object of the invention is to provide an improved means for predicting an increased likelihood of bearing a Down's syndrome child.

That these and other objects have been achieved will be seen from the within specification, including the disclosures herein of a preferred embodiment and its use, the claims, and the figures, in which FIG. 1 is a photograph showing crossed immunoelectrophresis patterns as obtained by the invention on controls.

Figure 2:
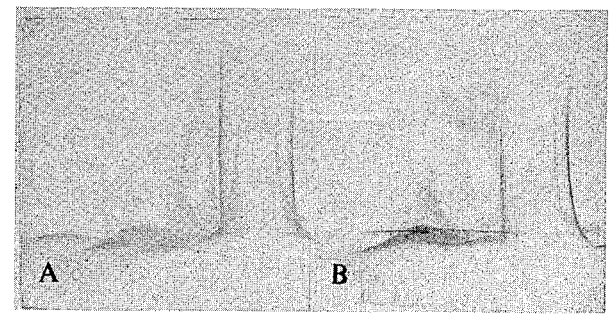

FIG. 2 is a photograph showing crossed immunoelectrophoresis patterns obtained by the invention on experimental subjects.

PRACTICE OF THE PREFERRED METHOD AND USE OF THE INVENTION

The following are illustrative experimental details of the invention as actually practiced. The general method of Weeke (Weeke, B. Crossed Immunoelectrophoresis. In *A Manual of Quantitative Immunoelectrophoresis. Methods and Applications,* N. H. Axelsen, J. Kroll, B. Weeke, Eds., *Scand J Immunol* 2 (suppl 1), 1973, pp. 47–59) was used; that reference is specifically incorporated into this disclosure.

A. Materials

1. Equipment

For all electrophoresis procedures a Gelman (Ann Arbor, Mich. 48106) power supply, Model 38206, and a Gelman deluxe electrophoresis buffer chamber were used.

Another electrophoresis chamber was constructed of Plexiglas having dimensions of 37.5 cm by 30.5 cm. Platinum wire was used for electrodes. The lid was slanted to prevent moisture from dropping onto the gel surface during electrophoresis. An immunoelectrophoresis kit (Gelman, Product 51446) was employed.

Ultra Wicks (Biorad Laboratories, Richmond, Calif. 94804), 20.0 cm by 25.0 cm were cut to an appropriate size to provide sufficient gel-buffer contact during two dimensional electrophoresis.

Two sizes of glass plates were used for two dimensional immunoelectrophoresis procedures; 8.3 cm by 10.2 cm precleaned, projector slide cover glass (Kodak, Rochester, N.Y, 14650) and 5.0 cm by 5.0 cm plates (Biorad).

A ten microliter glass syringe (Hamilton Co., Reno, Nev. 89501) was fitted with a 2.5 cm piece of tygon microbore tubing (ID 0.1 mm, Norton, Akron, Ohio 44308) and used for each sample application.

2. Reagents

Tricine (N-tris(hydroxymethyl)methyl-glycine) and Tris (Trizma®Base, 2-amino-2-(hydroxymethyl)-1,3-propanediol), both of greater than 99 percent purity, were purchased from Sigma Chemical Company, St. Louis, Mo. 63178.

®Agarose, electroendosmosis, $m_r = 0.16–0.19$, (Marine Colloids Division, FMC Corporation, Rockland, Me. 04841) was used for electrophoresis gel medium.

Bromophenol Blue (Matheson, Coleman and Bell, Norwood, Ohio 45212) was used as a marker dye.

The following antisera were rabbit antisera to human serum proteins and purchased from Calbiochem-Behring Corp., LaJolla, Calif. 92037:

| antibody to | lot number |
| --- | --- |
| whole human serum | 009639 |
| | 009916 |

Coomassie Brilliant Blue R-250 (Biorad) was used for the protein stain.

All other chemicals used in the preparations of buffers, and staining, rinsing, and washing solutions were reagent grade and purchased from Fisher Scientific Co., Pittsburgh, Pa. 15219.

Double-distilled, deionized water was used in the preparation of all solutions.

B. Procedures

Tris-Tricine buffer (Monthony, J. F., Wallace, E. G., Allen, D. M. A Non-barbital Buffer for Immunoelectrophoresis and Zone Electrophoresis in Agarose Gels. *Clin Chem* 24, 1825–1827 (1978)) was prepared before each electrophoretic assay. Formulation was as follows: 9.8 g Tris, 4.30 g Tricine, 0.016g calcium lactate, and 0.2 g sodium azide were dissolved and diluted to one liter with water. The pH was 8.6 at 20° C., adjusted if necessary.

One gram agarose in 100 mL of buffer was heated at 90° C. until the solution became clear and then allowed to cool to 60° C. At this point 0.04 mL of a two percent aqueous solution of Bromophenol Blue was added to the agarose solution to serve as a marker dye during electrophoresis.

Twenty mL of agarose were poured onto each of two 8.3 cm by 10.2 cm glass plates that had been positioned on a leveling table. After the agarose gelled, five 1 mm diameter wells were punched out on each plate along the length of the plates, each 2.7 cm from the edge of the plate and 1.0 cm from the next well·(FIG. 3). A 1 µL sample was applied to each well.

The two plates were placed into an electrophoresis chamber containing 900 mL of buffer (450 mL on each side). Electrophoresis parameters for the first dimension were 17.6 volts per cm for two hours. Upon completion of the first dimension electrophoresis, the plates were removed. Gel strips, 5.0 cm by 1.3 cm, were cut and transferred to 5.0 cm by 5.0 cm glass plates.

Antibody-containing gel was prepared by mixing 0.7 mL of antiserum with 35 mL of the one percent agarose solution at 60° C. Three mL of this antibody gel were poured onto each 5.0 cm by 5.0 cm small plate.

Five of these plates were placed into each of two electrophoresis chambers which were connected in parallel to the power supply. A potentiometer in series with one of the chambers was adjusted so that current flow in the chambers was equal.

Electrophoresis in the second dimension was performed at 8 volts per cm for 25 hours.

After the second migration was completed, the plates were removed, covered with moistened filter paper and allowed to air dry at room temperature.

The dry plates were stained with Coomassie Brilliant Blue R-250 protein stain (0.1 percent solution in 45:45:10 v/v/v methanol:water:acetic acid) for 20 to 30 minutes, then rinsed in three successive methanol:water:acetic acid (45:45:10 v/v/v) solutions for 20 to 30 minutes each.

The background cleared slides were visually inspected for the presence or absence of the Down's syndrome protein by using a light box.

C. Application of the Method and Study of Its Utility

The modified crossed immunoelectrophoresis technique was employed to further investigate the Down's syndrome protein observed by Kerkay et al. (Kerkay, J., Zsako, S., Kaplan, A. R. Immunoelectrophoretic Patterns Associated with Mothers of Children Affected with G -trisomy (Down's Syndrome). *Am J Mental Deficiency* 75, 729–732 (1971)) and to develop a method whereby the immunoelectrophoresis patterns of men and women might be more easily evaluated for the presence of this protein.

Samples received were serum specimens of volunteers who has their blood drawn by personnel at a hospital, clinic, or doctor's office.

Assays were performed within three or four days of receipt and repeated twice thereafter; once one or two weeks later and again two or three months later. No differences in sample patterns were noted upon repetition. Sample showed signs of degradation after three months of refrigeration at 4° C. and were not used thereafter.

Initially, samples were compared by standard immunoelectrophoresis in order to verify the work of Kerkay et al. that there was a difference between the serum patterns of mothers of Down's syndrome children and mothers of unaffected children. Following immunoelectrophoresis, samples were tested by crossed immunoelectrophoresis. As the study progressed, the initial immunoelectrophoresis step was eliminated.

During each crossed immunoelectrophoresis experiment, both Down's and normal serum controls were run. Each subject's resulting pattern was compared to the controls for evaluation.

FIG. 1 illustrates the positive and negative control crossed immunoelectrophoresis patterns for the Down's syndrome protein. The positive pattern (D) shows a protein peak (indicated by an arrow) migrating between the gamma globulins and albumin and considered to be in the pre-beta region. The position occupied by the peak in the Down's positive pattern is vacant in the normal pattern.

Although the normal pattern does not show the Down's syndrome protein, it does show a protein peak that migrates with the beta globulins and is not present in the positive pattern. This peak is indicated by an arrow on the negative pattern (N) in FIG. 1.

Thus, only when the Down's syndrome protein is present is a positive result indicated. FIG. 2 shows an example of the crossed immunoelectrophoresis results of a subject (A) positive for and a subject (B) negative for the Down's syndrome protein.

The sera of seventy-one women and twenty-six men were tested for the presence of the Down's syndrome protein.

The women tested ranged in age from 16 to 65 years at the time of the test. Ages at the time of birth of the affected child for twenty-eight mothers of Down's syndrome children ranged from 18 to 40 years. The average age was 28.3 years. The Down's syndrome children in all of these cases were of the trisomy 21 type.

The forty-three women having either no children or only children not affected with Down's syndrome ranged in age from 16 to 65 years at the time of the test.

TABLE I

Summary Of CIE Results For Individuals

| WOMEN WITH TRISOMY 21 CHILDREN | |
|---|---|
| POSITIVE | 18 (64.3%) |
| NEGATIVE | 10 (35.7%) |
| TOTAL | 28 |
| WOMEN WITH UNAFFECTED OR NO CHILDREN | |
| POSITIVE | 7 (16.3%) |
| NEGATIVE | 36 (83.7%) |
| TOTAL | 43 |
| MEN WITH TRISOMY 21 CHILDREN | |
| POSITIVE | 5 (41.7%) |
| NEGATIVE | 7 (58.3%) |
| TOTAL | 12 |
| MEN WITH UNAFFECTED OR NO CHILDREN | |
| POSITIVE | 2 (14.3%) |
| NEGATIVE | 12 (85.7%) |
| TOTAL | 14 |

Table I is a summary of the crossed immunoelectrophoresis results of individual volunteers. Of the mothers of trisomy 21 children, 64.3 percent gave positive results and 35.7 percent gave negative results.

Of the women with unaffected or no children, 83.7 percent gave negative results; only 16.3 percent gave positive results.

Of the fathers of trisomy 21 children, 41.7 percent gave positive results; 58.3 percent gave negative results.

Of the men with unaffected or no children, 14.3 percent gave positive results and 85.7 percent gave negative results.

For both mothers and fathers of trisomy 21 children the difference between the average age at birth of the affected child for the positive group and the average age for the negative group was insignificant ($t = 3.29$, 99.9 percent confidence interval).

TABLE II

Summary Of CIE Results For Couples

| PARENTS OF TRISOMY 21 CHILDREN | |
|---|---|
| BOTH POSITIVE | 3 (25.0%) |
| BOTH NEGATIVE | 7 (58.3%) |
| EITHER POSITIVE | 2 (16.7%) |

TABLE II-continued

| Summary Of CIE Results For Couples | |
|---|---|
| PARENTS OF UNAFFECTED CHILDREN | |
| BOTH POSITIVE | 1 (11.1%) |
| BOTH NEGATIVE | 8 (88.9%) |
| EITHER POSITIVE | 0 |
| COUPLES WITH NO CHILDREN | |
| BOTH POSITIVE | 1 |
| BOTH NEGATIVE | 1 |
| EITHER POSITIVE | 0 |

Table II is a summary of the crossed immunoelectrophoresis results of couples who volunteered. Twelve who are parents of trisomy 21 children were tested. In three cases (25 percent) both parents gave positive CIE results; in seven cases both parents gave negative results.

Two trisomy 21 children were tested. Both gave negative CIE results. In one case the parents were not tested; in the other case both parents gave negative results.

The results of the study of volunteers demonstrate that detection of the Down's syndrome protein in the serum of a potential mother or father would indicate a high risk for parenting a Down's syndrome child.

Of the 97 volunteers tested for the presence of the Down's syndrome protein, 28 were mothers of trisomy 21 children and 12 were fathers of trisomy 21 children. The mothers' average age at the time of birth of the affected children was 28.3 years; the fathers' average age was 29.7 years. Although the number of mothers and fathers tested is small, the average ages compare well with the average ages of 28.4±7.9 years for mothers and 28.4±3.6 years for fathers of trisomy 21 children cited by Mikkelsen et al (Mikkelsen, M., Hallberg, A., Poulsen, H. Maternal and Paternal Origin of Extra Chromosome in Trisomy 21. *Hum Genet* 32, 17–21 (1976)). Thus, the population of mothers and fathers of affected children tested for the Down's syndrome protein is representative of the total population of mothers and fathers of trisomy 21 children. The control groups are presumed to be representative of the total population of parents of unaffected children and potential parents.

TABLE III

| | Relationship Of Age* To CIE Results: Parents Of Trisomy 21 Children | | | | | | |
|---|---|---|---|---|---|---|---|
| | MOTHERS | | FATHERS | | PARENTS | | |
| AGE GROUP | positive | negative | positive | negative | both positive | both negative | either positive |
| less than 20 years | 2 | 0 | 0 | 0 | 0 | 0 | 0 |
| 20–29 | 8 | 4 | 3 | 3 | 3+ | 3 | 0 |
| 30–39 | 9 | 6 | 3 | 4 | 1 | 4 | 2 |
| 40– | 1 | 0 | 0 | 0 | 0 | 0 | 0 |

*Age at birth of Down's syndrome child. Multiple births are counted individually and include Down's syndrome fetuses that were not born.

Table III shows the relationship between parental age at the time of birth of the trisomy 21 child and the presence or absence of the Down's syndrome protein. Numbers in this table represent trisomy 21 births rather than parents, since there were multiple births in which the age range for the parent was different for each birth.

Although the percentages of positive CIE results, indicating the presence of the Down's syndrome protein, in mothers' age groups less than 20 years and 40 years and older are 100 percent, the number of mothers in these age groups who were tested is too small to permit making any conclusions from that observation.

The percentages of positive CIE results in mothers' age groups 20 to 29 years and 30 to 39 years are 66 pe and 60 percent, respectively. These percentages do not differ significantly from the overall percentage of 64.3 percent presented in Table I. Likewise, for fathers in the same age groups, 20 to 29 years and 30 to 39 years, the percentage of positive CIE results, 50 percent and 43 percent, respectively, do not appreciably differ from the overall percentage of 41.7 percent also shown in Table I.

Table III also shows the CIE results when both parents of trisomy 21 children were tested. Again, the proportions of positive results and negative results are nearly the same in the two age groups discussed for mothers and fathers individually. Fifty percent of the parents in the 20 to 29 years age group and 43 percent of the parents in the 30 to 39 years age group gave positive results indicating the presence of the Down's syndrome protein in both or either of the parents.

TABLE IV

| | Relationship Of Age* To CIE Results: Parents Of Unaffected Children | | | | | | |
|---|---|---|---|---|---|---|---|
| | MOTHERS | | FATHERS | | PARENTS | | |
| AGE GROUP | positive | negative | positive | negative | both positive | both negative | either positive |
| less than 20 years | 0 | 0 | 0 | 0 | 0 | 0 | 0 |
| 20–29 | 1 | 1 | 0 | 0 | 0 | 0 | 0 |
| 30–39 | 1 | 12 | 1 | 5 | 1 | 5+ | 0 |
| 40– | 3 | 4 | 0 | 2 | 0 | 1 | 0 |

*Age at time of test.
+Father in one set of parents was 51 years old.

TABLE V

| | Relationship Of Age* To CIE Results: Women and Men With No Children | | | | | | |
|---|---|---|---|---|---|---|---|
| | WOMEN | | MEN | | COUPLES | | |
| AGE GROUP | positive | negative | positive | negative | both positive | both negative | either positive |
| less than 20 years | 0 | 3 | 0 | 0 | 0 | 0 | 0 |
| 20–29 | 0 | 4 | 0 | 3 | 0 | 1 | 0 |
| 30–39 | 2 | 7 | 0 | 2 | 1+ | 2 | 2 |
| 40– | 0 | 4 | 1 | 0 | 0 | 0 | 0 |

*Age at test time.
+Male is 40 years old.

Tables IV and V show the relationship between the age at test time of parents with unaffected children and couples with no children, respectively, and the presence of the Down's syndrome protein. The majority of volunteers are in the 30 to 39 years age group. This is probably due to concern about the statistical age correlation to Down's syndrome. Of mothers and fathers of unaffected children, only 20 percent gave positive CIE results; one set of parents out of seven gave positive results. Of women and men with no children, only 11.5 percent gave positive results; one couple out of four gave positive results.

The delineation of the CIE results according to age presented in Tables III, IV and V indicates that: (1) The presence of the Down's syndrome protein in the serum of the parents of trisomy 21 children is not a function of age, since the percentages of mothers and fathers who were CIE positive are essentially the same for all age groups. (2) The presence of the Down's syndrome protein in the serum of men and women having unaffected or no children also is not a function of age below 40 years. Although there seems to be a trend to a greater percentage of positive results in the 40 years and older age group for mothers of unaffected children (Table IV), this is not the case for women with no children. (Only one 40 year old mother of a trisomy 21 child was tested.)

The results of the CIE tests done on the volunteers clearly demonstrate a correlation of a positive CIE result, the presence of the Down's syndrome protein, to the birth of a trisomy 21 child. Since the protein has been found in the sera of men as well as in the sera of women who have not had a Down's syndrome pregnancy, its presence is not a consequence of that pregnancy. Therefore, the testing of men and women for the Down's syndrome protein can have predictive value.

FURTHER DISCLOSURE OF THE INVENTION

The aim of the improved method of the invention is to separate the Down's syndrome protein from the other serum proteins so it may be visualized. The original procedure of Weeke does not achieve this aim satisfactorily.

One of the principal advantages of the invention is that a very small sample size is used. This aids resolution. In our experiments sample sizes of 1 to 4 microliters were effectively employed; the optimal size appears to be about 1 $\mu$l.

The gel antiserum concentration used was much lower than in Weeke's method. A range of 2.25 to 3.25 $\mu$l per cm$^2$ is presently preferred. The agarose concentration should be about 1.0% but it may be as high as 2%.

The first dimension voltage can be about the same as Weeke's (120–160 volts). We prefer to use 150 volts for about two hours. The second dimension voltage is very much greater than that used by Weeke. It will be clear to those skilled in the art that the time period for application of the second voltage will be shorter as the voltage is greater. Electrophoresis is continued for a time sufficient to achieve the resolution desired. The preferred range is 30 to 45 volts (6 to 9 volts per cm of gel); for this range, a time range of 46 to 13 hours is presently used. If the second dimension voltage is substantially less than 6 volts per centimeter, the length of time required causes outward diffusion and less satisfactory peak separation. If it is substantially greater than 9 volts per cm, the heat generated in the electrophoretic chamber causes gel integrity to be sacrificed. A voltage of 40 volts (8 volts per cm) for 25 hours is presently thought to be optimal.

Finally the use of Tris-Tricine buffer instead of a barbital buffer in the gels eliminates the need for a saline wash, provides sharper patterns, and is less expensive.

The invention has been described in detail with particular emphasis on the preferred embodiments, but it should be understood that variations and modifications within the scope and spirit of the invention may occur to those skilled in the art to which the invention pertains.

What is claimed is:

1. A method of determining the existence of a greater than normal potential of a woman's bearing a Down's syndrome child, said method comprising obtaining a sample of said woman's blood serum;

electrophoresing said sample through a first gel in a first direction at a first voltage and for a first time period sufficient to produce a track of separated proteins in said first gel;

electrophoresing a portion of said first gel containing all of said track at a second voltage lying in the range of 6 to 9 volts per centimeter, in a second direction perpendicular to said track through a second gel prepared from a buffer solution and agarose and containing a concentration of antiserum directed against Down's syndrome protein (DSP), which said antiserum reacts with said Down's syndrome protein to generate a DSP precipitin arc in the gamma-A region, for a sufficient time to generate a series of precipitin peaks in said gamma-A region representing the said separated proteins, said concentration of said antiserum lying in the range of 2.25 to 3.25 microliters per square centimeter of said second gel, said second gel being 0.12 cm thick; and determining whether a DSP precipitin arc has been generated in the same gamma-A region, the presence of said arc indicating the presence of said greater than normal potential.

2. A method of determining the existence of a greater than normal potential of a man's fathering a Down's syndrome child, said method comprising obtaining a sample of said man's blood serum;

electrophoresing said sample through a first gel in a first direction at a first voltage and for a first time period sufficient to produce a track of separated proteins in said first gel;

electrophoresing a portion of said first gel containing all of said track at a second voltage lying in the range of 6 to 9 volts per centimeter, in a second direction perpendicular to said track through a second gel prepared from a buffer solution and agarose and containing a concentration of antiserum directed against Down's syndrome protein (DSP), which said antiserum reacts with said Down's syndrome protein to generate a DSP precipitin arc in the gamma-A region, for a sufficient time to generate a series of precipitin peaks in said gamma-A region representing the said separated proteins, said concentration of said antiserum lying in the range of 2.25 to 3.25 microliters per square centimeter of said second gel, said second gel being 0.12 cm thick; and determining whether a DSP precipitin arc has been generated in the said gamma-A region, the presence of said arc indicating the presence of said greater than normal potential.

* * * * *